(12) United States Patent
Savilahti et al.

(10) Patent No.: US 7,172,882 B2
(45) Date of Patent: Feb. 6, 2007

(54) METHOD AND MATERIALS FOR PRODUCING DELETION DERIVATIVES OF POLYPEPTIDES

(75) Inventors: Harri Savilahti, Helsinki (FI); Ville Tieaho, Haarajoki (FI)

(73) Assignee: Finnzymes Oy, Espoo (FI)

( * ) Notice: Subject to any disclaimer, the term of this patent is extended or adjusted under 35 U.S.C. 154(b) by 0 days.

(21) Appl. No.: 10/511,327

(22) PCT Filed: Apr. 14, 2003

(86) PCT No.: PCT/FI03/00285

§ 371 (c)(1),
(2), (4) Date: Mar. 30, 2005

(87) PCT Pub. No.: WO03/087370

PCT Pub. Date: Oct. 23, 2003

(65) Prior Publication Data

US 2005/0208616 A1      Sep. 22, 2005

(30) Foreign Application Priority Data

Apr. 18, 2002   (FI) ................................. 20020746

(51) Int. Cl.
*C12P 19/34*   (2006.01)
*C12N 15/66*   (2006.01)
(52) U.S. Cl. ............... 435/91.1; 435/94.41; 435/320.1
(58) Field of Classification Search .................... None
See application file for complete search history.

(56) References Cited

U.S. PATENT DOCUMENTS 5,948,622 A      9/1999    Reznikoff et al.

OTHER PUBLICATIONS

Coros et al. J. Mol. Bio. (2001) 310, 299-309.*
York et al. Nucleic Acids Research 1998 vol. 26 No. 8.*
Dona York et al., Nucleic Acids Research, vol. 26, No. 8, 1998, pp. 1927-1933.
Saija Haapa et al., Nucleic Acids Research, vol. 27, No. 13, 1999, pp. 2777-2784.
Insuk Lee et al., J. Mol. Biol. vol. 314, 2001, pp. 433-444.
Louise Chang Laurent et al., Journal of Virology, vol. 74, No. 6, 2000 pp. 2760-2769.
Finbarr Hayes et al., Trends in Microbiology, vol. 8, No. 12, 2000, pp. 571-577.
Colin J. Coros et al., J. Mol. Biol., vol. 310, 2001, pp. 299-309.

* cited by examiner

*Primary Examiner*—James Ketter
(74) *Attorney, Agent, or Firm*—Birch, Stewart, Kolasch & Birch, LLP

(57) ABSTRACT

The present invention describes an in vitro transposition-based methodology for generation of deletion derivatives of polypeptides. An artificial transposon containing at least partly within its transposon ends a modification with translation stop codons in three reading frames is provided. In the method, transposition complexes are assembled using the modified transposon and essentially random integrations into the target plasmid, containing a polypeptide coding nucleic acid of interest, are recovered as a plasmid pool. Subsequent manipulation steps including restriction enzyme digestions and ligation result in pools of mutant clones from which deletion derivatives of a polypeptide coding nucleic acid of interest and its respective deletion polypeptides could be produced.

11 Claims, 7 Drawing Sheets

METHOD AND MATERIALS FOR PRODUCING DELETION DERIVATIVES OF POLYPEPTIDES

The present invention relates to genetic engineering and especially in vitro transposition. The invention describes a method and materials for producing deletion derivatives of polypeptide coding nucleic acids. In particular, the invention provides means for efficient generation of C-terminal deletions of polypeptides by the use of a modified transposon with translation stop codons in all three reading frames. The invention further provides a kit for producing said deletion derivatives.

BACKGROUND OF THE INVENTION

Thousands of different types of protein species constitute a major molecular component of cellular life. These molecules are composed of amino acid chains, the sequence of which is encoded by the genes in the organism's DNA. The protein function can be diverse and specific functions have been evolved for different cellular demands. Native wild type protein molecules can obviously be studied for their function biochemically and genetically. The data thus obtained can be informative but very often such information is relatively limited. A better description of protein function can be gained through mutational analysis in which various types of mutations are introduced into the protein primary sequence and the mutated proteins are then analyzed for their function. With current recombinant DNA technology (Sambrook et al. 1989, Sambrook and Russell 2001), generation of mutations is relatively easy and therefore mutational analysis of proteins has become a standard in functional studies of proteins.

In principle, three different types of mutations can be introduced into a protein sequence (i) substitutions, (ii) insertions, and (iii) deletions. In a substitution mutation, a particular amino acid (or an amino acid stretch) in a protein is changed to another (or to another amino acid stretch of same length). In an insertion, an amino acid or a stretch of amino acids is added to the protein thus increasing the length of the amino acid chain. In a deletion mutation, an amino acid or a stretch of amino acids are eliminated from the protein sequence and thus the protein becomes smaller in size.

Various mutagenesis methods are currently available for generation of different types of mutations. These methods are typically straightforward to use. However, in most of the cases the wanted mutations are generated one by one and, therefore, their construction is time-consuming and labor-intensive. It would be desirable if a number of mutations could be generated simultaneously. For certain types of insertion mutations this type of approach has been described (Hayes and Hallet 2000). However, an efficient method for simultaneous generation of substitution and deletion mutations is still lacking.

One of the in vitro transposition systems we utilised for the present invention was a bacteriophage Mu-derived transposition system that has recently been introduced (Haapa et al. 1999a) and shown to function efficiently in many types of molecular biology applications (Wei et al. 1997, Taira et al. 1999, Haapa et al 1999ab, Vilen et al. 2001). Mu transposition proceeds within the context of protein-DNA complexes that are called DNA transposition complexes or transpososomes (Mizuuchi 1991, Savilahti et al. 1995). These complexes are assembled from a tetramer of MuA transposase protein and Mu-transposon-derived DNA-end-segments (i.e. transposon end sequences recognised by MuA) containing MuA binding sites. When the complexes are formed they can react in divalent metal ion-dependent manner with any target DNA and splice the Mu end segments into the target (Savilahti et al 1995). In the simplest case, the MuA transposase protein and a short 50 bp Mu right-end (R-end) fragment are the only macromolecular components required for transpososome assembly (Savilahti et al. 1995, Savilahti and Mizuuchi 1996). Analogously, when two R-end sequences are located as inverted terminal repeats in a longer DNA molecule, transposition complexes form by synapsing the transposon ends. Target DNA in Mu DNA transposition in vitro can be linear, open circular, or supercoiled (Haapa et al. 1999a).

Mu transposition complex, the machinery within which the chemical steps of transposition take place, is initially assembled from four molecules of MuA transposase protein that first bind specific binding sites in the transposon ends (FIGS. 5A and 5B). The 50 bp Mu right end DNA segment contains two of these binding sites (they are called R1 and R2 and each of them is 22 bp long, Savilahti et al. 1995). When two ends, each bound by two MuA monomers, meet, the transposition complex is formed through conformational changes, the nature of which are not fully understood because of a lack of atomic resolution structural data on Mu transpososomes. However, the assembly of the minimal Mu transpososome is clearly dependent upon the correct binding of MuA transposase to Mu ends of the donor DNA. Thus, modifications in the conserved nucleotide sequence of transposon ends (e.g. R1 and R2 sequences in Mu R-end) should potentially have a negative effect on the efficiency of the transposition since every altered nucleotide conceivably interferes with the MuA binding. It has been documented (Lee and Harshey 2001, Coros and Chaconas 2001) that the two last base pairs in the Mu transposon end can be modified without severe effect on transpososome function. However, no detailed analysis has been conducted for elucidation of the effects of modified R1 and R2 binding sites. In one example (Laurent et al. 2000) a NotI restriction site was engineered close to the transposon end that changed one base pair in the R1 sequence. In vivo studies indicate that within the R1 and R2 sequences mutations generally have negative effects on transposition efficiency (Groenen et al. 1985, 1986). In addition, these effects are typically additive.

SUMMARY OF THE INVENTION

In this invention we describe a general methodology for making deletion derivatives of polypeptides using in vitro DNA transposition system. The method of the invention can be used to generate a number of deletion-derivatives of polypeptide coding nucleic acids simultaneously and with ease.

We utilised modified transposons that allowed us to generate C-terminal deletion derivatives of polypeptides. The methodology should be applicable to any protein, the encoding nucleic acid sequence (e.g. a gene) of which is cloned in a plasmid or other DNA vector.

In one aspect, the invention features a transposon nucleic acid comprising a genetically engineered translation stop signal in three reading frames at least partly within a transposon end sequence, or preferably within transposon end binding sequence, recognised by a transposase.

In various embodiments the transposon nucleic acid of the invention may contain a selectable marker and/or reporter gene. In one preferable embodiment the transposon end sequence of said transposon nucleic acid is Mu end sequence recognised by MuA transposase. In one particular embodiment said Mu end sequence is Mu R-end sequence.

In another preferred embodiment of the invention the modified transposon is a Tn7-derived transposon.

In a second aspect, the invention provides a method for producing a deletion derivative of a polypeptide coding nucleic acid comprising the steps of:

(a) performing a transposition reaction in the presence of the transposon nucleic acid of the invention and a target nucleic acid containing a polypeptide coding nucleic acid of interest, (b) recovering a target nucleic acid having said transposon nucleic acid incorporated in said polypeptide coding nucleic acid.

In a preferred embodiment the method of the invention further comprises a step of (c) expressing said polypeptide coding nucleic acid having said transposon nucleic acid incorporated.

In a third aspect, the invention provides a kit for producing deletion derivatives of polypeptide coding nucleic acids. The kit comprises the transposon nucleic acid of the invention.

In a fourth aspect, the invention features use of the transposon nucleic acid of the invention for producing deletion derivatives of polypeptide coding nucleic acids.

The term "transposon", as used herein, refers to a nucleic acid segment, which is recognised by a transposase or an integrase enzyme and which is essential component of a functional nucleic acid-protein complex capable of transposition (i.e. a transpososome).

The term "transposase" used herein refers to an enzyme, which is an essential component of a functional nucleic acid-protein complex capable of transposition and which is mediating transposition. The term "transposase" also refers to integrases from retrotransposons or of retroviral origin.

The expression "transposition reaction" used herein refers to a reaction wherein a transposon inserts into a target nucleic acid. Essential components in a transposition reaction are a transposon and a transposase or an integrase enzyme or some other components needed to form a functional transposition complex. The method and materials of the present invention are exemplified by employing in vitro Mu transposition (Haapa et al. 1999ab and Savilahti et al. 1995) or transposition system of Tn7 (Craig, 1996). Other transposition systems can be used as well. Examples of such systems are Ty1 (Devine and Boeke, 1994, and International Patent Application WO 95/23875), Tn 10 and IS 10 (Kleckner et al. 1996), Mariner transposase (Lampe et al., 1996), Tc1 (Vos et al., 1996, 10(6), 755–61), Tn5 (Park et al., 1992), P element (Kaufman and Rio, 1992) and Tn3 (Ichikawa and Ohtsubo, 1990), bacterial insertion sequences (Ohtsubo and Sekine, 1996), retroviruses (Varmus and Brown 1989) and retrotransposon of yeast (Boeke, 1989).

The term "transposon end sequence" used herein refers to the conserved nucleotide sequences at the distal ends of a transposon. The transposon end sequences are responsible for identifying the transposon for transposition.

The term "transposon end binding sequence" used herein refers to the conserved nucleotide sequences within the transposon end sequence whereto a transposase specifically binds when mediating transposition.

The term "target nucleic acid" used herein refers to a nucleic acid molecule containing a protein coding nucleic acid of interest.

The term "translation stop signal" used herein refers to the genetic code, which contains three codon triplets (UAA, UAG, UGA) for terminating the polypeptide chain production during protein synthesis in a ribosome. In a DNA strand the corresponding stop signal triplets are TAA, TAG and TGA.

The term "reading frame" used herein refers to any sequence of bases in DNA or RNA that codes for the synthesis of either a protein or a component polypeptide. The point of initiation of reading determines the frame, i.e. the way in which the bases will be grouped in triplets as required by the genetic code.

The term "genetic engineering" used herein refers to molecular manipulation involving the construction of artificial recombinant nucleic acid molecules.

The term "gene" used herein refers to genomic DNA or RNA that are translated into polypeptides.

DETAILED DESCRIPTION OF THE INVENTION

It has been published previously that protein engineering applications will benefit from Mu-based transposon strategies since it was established that any DNA sandwiched between Mu ends could be utilised as artificial transposons (Haapa et al. 1999a). In, principle insertion mutations (e.g. by addition of epitope tags or protein domains) and deletion mutations (by addition of translation stop codons) were foreseen with this strategy. However, introduction of a translation stop codon between transposon ends would leave a number of encoded amino acid residues into the protein's C-terminus. Given that an effective Mu end is about 50 bp in length, minimally this strategy would leave approximately 18 extra amino acids attached in the protein C-terminus. Extra amino acids may interfere with the protein function, therefore it would be better to add the stop codons as close as possible to the transposon end. By modifying the nucleotides of the Mu R-end (total of 7 nucleotides were changed, 5 of said nucleotides reside in Mu R1 sequence), we managed to place three stop codons in three reading frames very close to the Mu R-end resulting in transposons that still surprisingly retained their ability to form transposition complexes that were competent for transposition chemistry, i.e. they facilitated the integration of the transposon in vitro into a target plasmid. In essence, all the possible C-terminal deletion variants can be generated.

Figure 1:
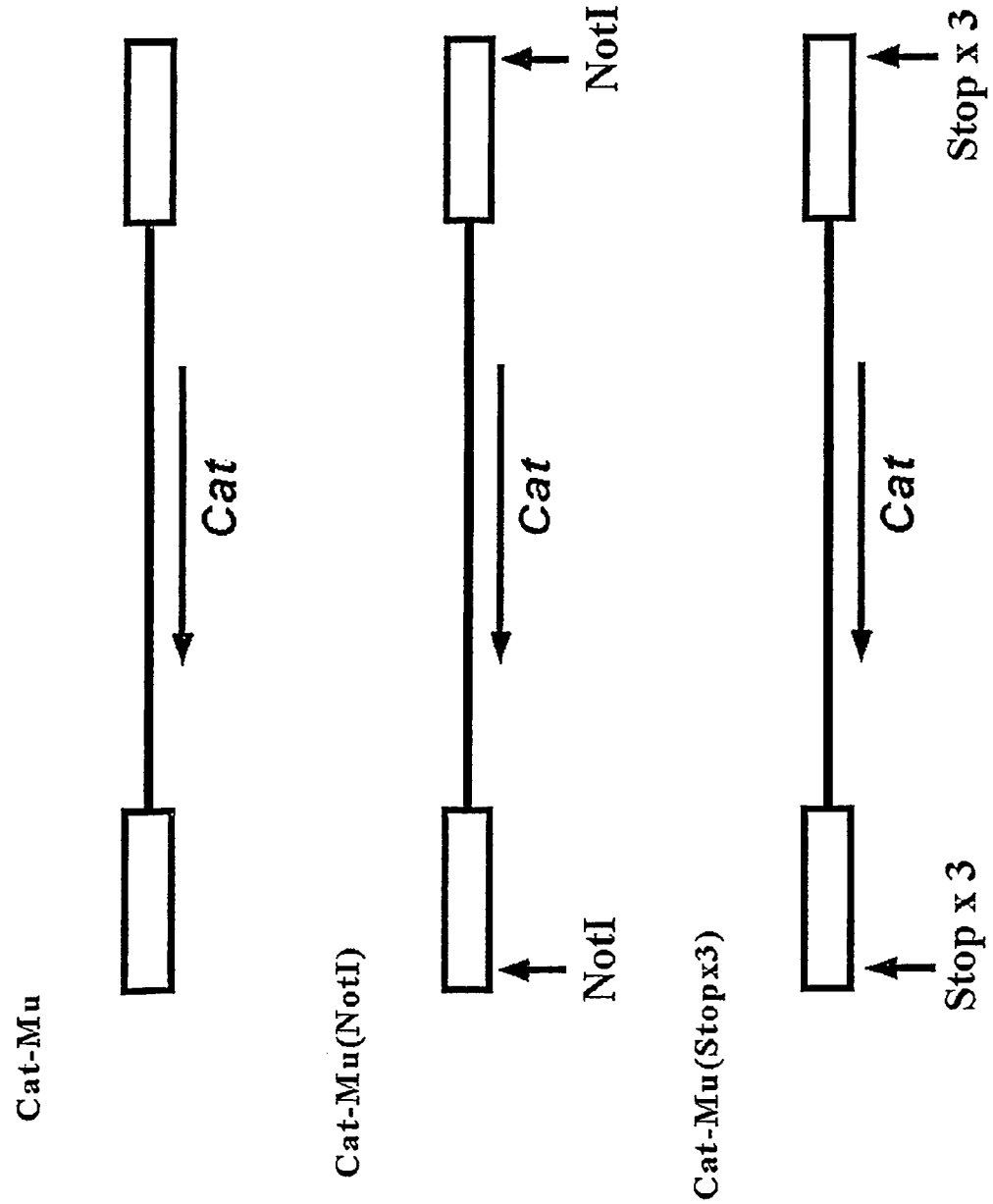
FIG. 1.
Cat-Mu transposons: Cat-Mu containing wild type Mu ends, Cat-Mu(NotI) containing Mu ends with engineered NotI restriction site, which design is described in Laurent et al. 2000, and Cat-Mu(Stop×3) containing Mu ends with engineered translation stop signal in three reading frames (SEQ ID NO:2). Transposon end sequences (i.e. inverted terminal repeats) are drawn as rectangles.
Figure 2:
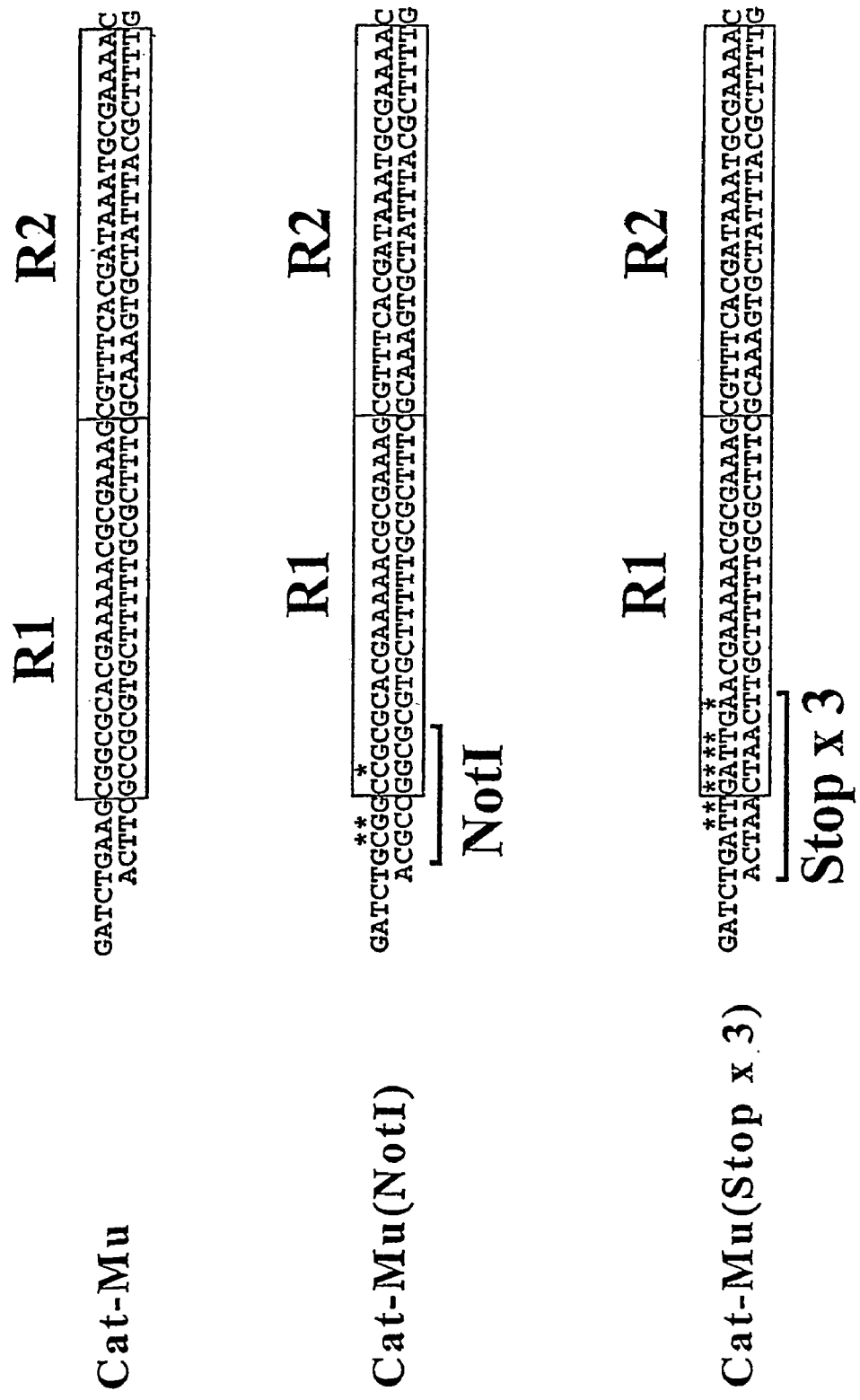
FIG. 2.
Transposon end sequences of Cat-Mu transposons: Cat-Mu transposon containing wild type Mu ends (SEQ ID NO: 3 and 14), Cat-Mu(NotI) containing Mu ends with engineered NotI restriction site described in Laurent et al. 2000 (SEQ ID NO: 4 and 15), and Cat-Mu(Stop×3) containing Mu ends with engineered translation stop signal in three reading frames (SEQ ID NO: 1 and 16). Asteriks (*) show modified nucleotides in the Mu ends of Cat-Mu(NotI) and Cat-Mu(Stop×3).

We designed an artificial Cat-Mu(Stop)-transposon (SEQ ID NO:2) conferring resistance to chloramphenicol and Tn7-Kan(Stop)-transposon (SEQ ID NO:7) conferring resistance to kanamycin. Both contained in their ends modified base pairs providing three stop codons in three reading frames (FIGS. 1 and 2). The gene mediating resistance to chloramphenicol is used as a selectable marker. The term "selectable marker" refers to a gene that, when carried by a transposon, alters the ability of a cell harboring the transposon to grow or survive in a given growth environment relative to a similar cell lacking the selectable marker. The transposon nucleic acid of the invention preferably contains a positive selectable marker. A positive selectable marker, such as an antibiotic resistance, encodes a product that enables the host to grow and survive in the presence of an agent, which otherwise would inhibit the growth of the organism or kill it. The transposon nucleic acid of the invention may also contain a reporter gene, which can be any gene encoding a product whose expression is detectable and/or quantitatable by immunological, chemical, biochemical, biological or mechanical assays. A reporter gene product may, for example, have one of the following attributes: fluorescence (e.g., green fluorescent protein), enzymatic activity (e.g., luciferase, lacZ/β-galactosidase), toxicity (e.g., ricin) or an ability to be specifically bound by a second molecule (e.g., biotin). The use of markers and reporter genes in prokaryotic and eukaryotic cells is well-known in the art. In a preferred embodiment the transposon nucleic acid of the invention may also contain genetically engineered restriction enzyme sites. For example, the selectable marker gene within the transposon of the invention may influence the protein expression when a construct obtained by the method of the invention is inserted into a protein expression plasmid. It is therefore desirable to engineer a pair of unique restriction sites to flank the selectable marker gene. The marker can then be removed easily by the use of these sites and thus the final expression construct would not contain the marker gene.

Hence, one embodiment of the invention provides a transposon nucleic acid comprising a genetically engineered translation stop signal in three reading frames at least partly within a transposon end sequence, or preferably within transposon end binding sequence, recognised by a transposase (i.e. at least one conserved nucleotide of the end sequence has been modified, preferably two, three, four or more conserved nucleotides have been modified). Preferably, the transposon nucleic acid of the invention comprises Mu or Tn7 transposon sequence. More preferably the transposon nucleic acid of the invention comprises Mu R-end sequence, e.g., the sequence of SEQ ID NO:1 or SEQ ID NO:5 (Mu-R end sequence not including 5' overhang, which thus can vary). In a transposon end sequence of the transposon nucleic acid of the invention, translation stop signals of three reading frames are in 5'-to-3' direction, preferably in succession close to each other at a very end of a transposon, thus the three stop signals are as near as possible the flanking sequence after the transposon is incorporated into a target. Furthermore, the transposon end sequences, which participate in the assembly of the transpososome discussed above, can be different from each other or they can be in different nucleic acid molecules. Preferably, both transposon end sequences participating in the transpososome have similar sequences (i.e. they are located as inverted terminal repeats).

The transposon nucleic acid of the invention is exemplified here by transposons of Mu (Examples 1–3) or Tn7 (Example 4) system. However, a person skilled in the art understands that teachings of this invention can be utilised in other transposon systems as well.

Another embodiment of the invention is a method for producing a deletion derivative of a polypeptide coding nucleic acid comprising the steps of:
(a) performing a transposition reaction in the presence of a target nucleic acid containing a polypeptide coding nucleic acid (e.g. a gene) of interest and in the presence of a transposon containing a genetically engineered translation stop signal sequence in three reading frames at least partly within a transposon end sequence recognised by a transposase, (b) recovering a target nucleic acid having said transposon incorporated in said gene.

The transposition reaction (a) includes a transposon in a form of linear DNA molecule, transposase protein (e.g. MuA), and a target DNA as macromolecular components. Additionally, the transposition reaction contains suitable buffer components including $Mg^{2+}$ ions critical for chemical catalysis. Buffer components such as glycerol and DMSO (or related chemicals or solvents) somewhat relax the requirements for transposition reaction (Savilahti et al. 1995). Transposon DNA, in principle, can be of any length given that it in each end contain a transposon (e.g. Mu or Tn7) end sequence. Typically, target DNA is in a form of circular plasmid. However, any double-stranded DNA molecule more than 25 bp is expected to serve as efficient target molecule (Savilahti et al. 1995, Haapa-Paananen et al. 2002). In transposition reaction the reaction components are incubated together; during the incubation transposition complexes first form and then react with target DNA splicing the transposon DNA into target DNA. This process yields transposon integrations into target molecules. The stoichiometry of the reaction (excess target) generates target molecules each with a single integrated transposon. Most importantly, the integration site in each molecule can be different. Even though some sites in DNA are somewhat more preferred than others most of the phosphodiester bonds in DNA will be targeted (Haapa et al. 1999ab, Haapa-Paananen et al. 2002). In practice this means that the integration sites are selected essentially randomly.

In the Examples below deletion mutant libraries were planned to cover the gene of interest at least 10-fold, i.e. when the target gene was approximately 600 bp, the final pool should contain of a minimum of 6000 mutants. As a test protein we utilised 23 kDa yeast Mso 1 protein (Aalto et al. 1997). Those skilled in the art can easily design different strategies for mutant library construction as such strategies are well-known in the art (see, e.g., Sambrook et al. 1989, Sambrook and Russell 2001).

Figure 3:
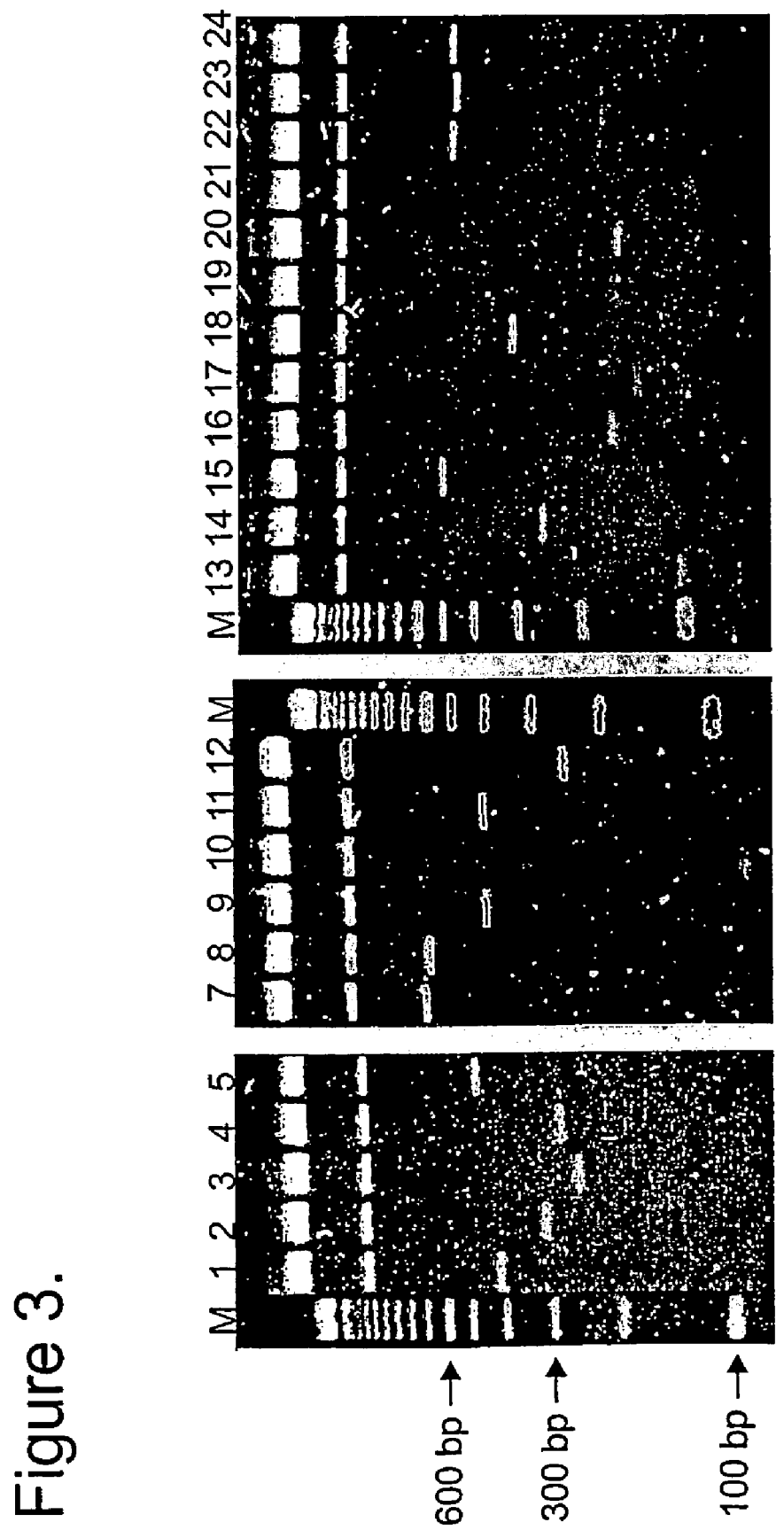
FIG. 3.
Analysis of C-terminal deletion variants on DNA level. Plasmids bearing Cat-Mu(Stop×3) transposon insertions (samples 1–24) were digested with BamHI, and they were analyzed on 1,8% agarose gels. The length of the shortest fragment of each digest corresponds roughly to the length of the deletion variant protein gene (0–~650 bp). M=DNA standards.

A mutant library was produced as described in Example 2. Target nucleic acids with a transposon insertion were isolated by size-selective preparative agarose gel electrophoresis. A person skilled in the art may design different isolation methods as such methods are well-known in the art (see, for example, Current Protocols in Molecular Biology, eds. Ausubel et al, John Wiley & Sons: 1992). We screened individual deletion mutants by restriction analysis (FIG. 3). This analysis demonstrates that in the library, there are variants of different sizes. A person skilled in the art can easily utilise different screening techniques. The screening step can be performed, e.g., by methods involving sequence analysis, nucleic acid hybridisation, primer extension or antibody binding. These methods are well-known in the art (see, for example, Current Protocols in Molecular Biology, eds. Ausubel et al, John Wiley & Sons: 1992).

We sequenced 23 C-terminal mutants derived from Example 2. All the mutants carried the translation stop codons in three reading frames.

Figure 4:
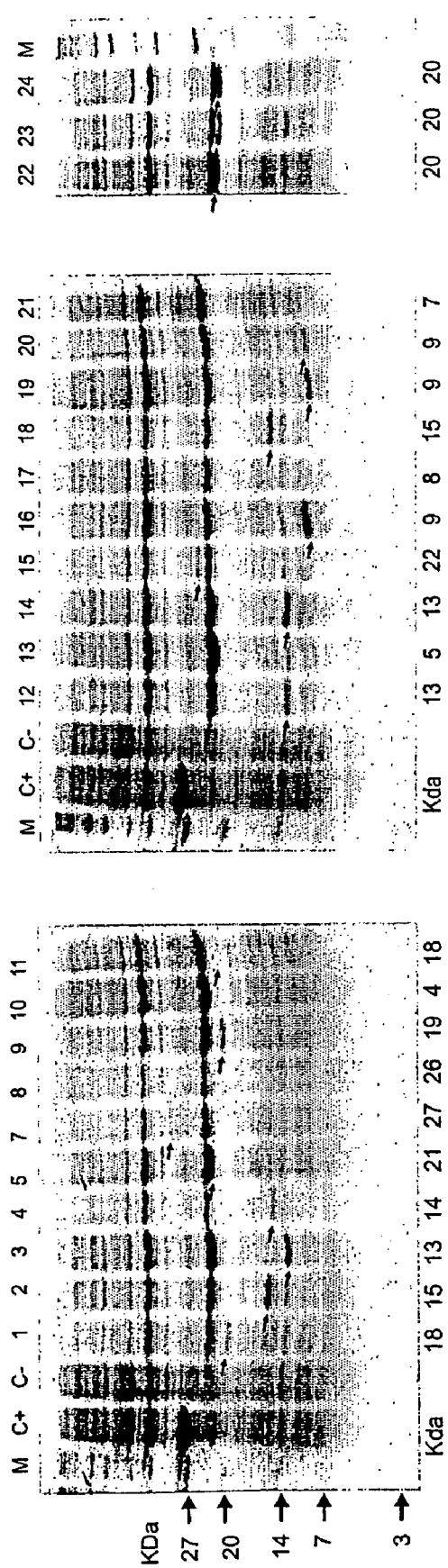
FIG. 4.
Analysis of C-terminal deletion variants on protein level. The sizes of the deletion variant proteins, as predicted by sequencing analysis, are marked below each lane as kilodaltons. M=molecular weight standard, $C^+$=positive control, $C^-$=negative control. Predicted deletion variant protein products are pointed out by arrows.
Figure 5A:
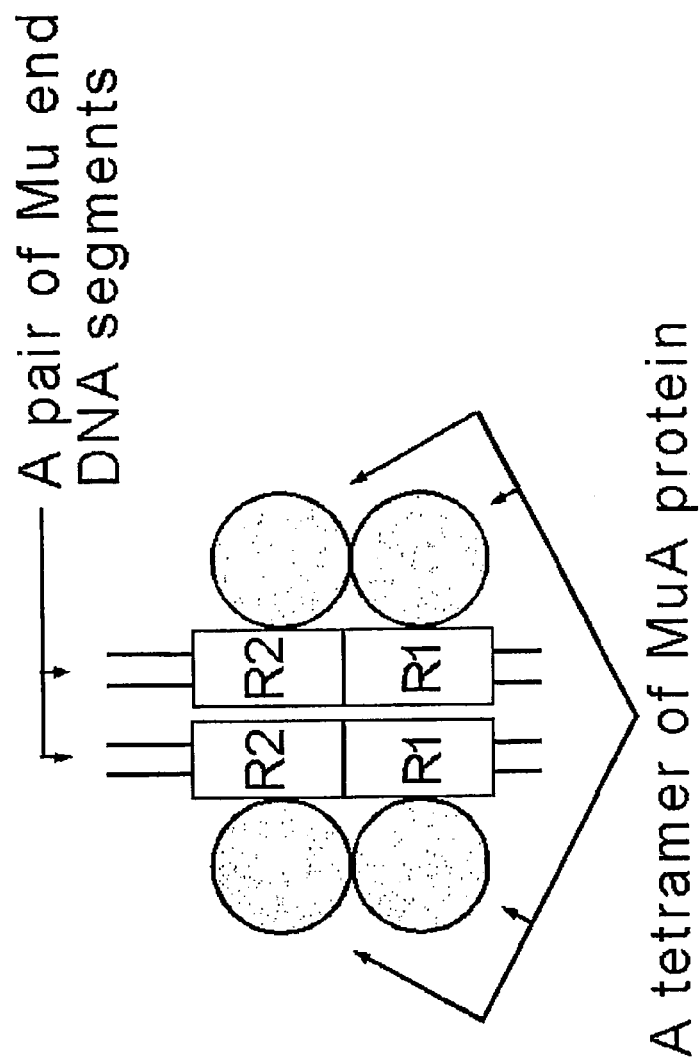
FIGS. 5A and 5B
5A, Mu transposition complex. 5B, the assembly of Mu transposition complex.
Figure 5B:
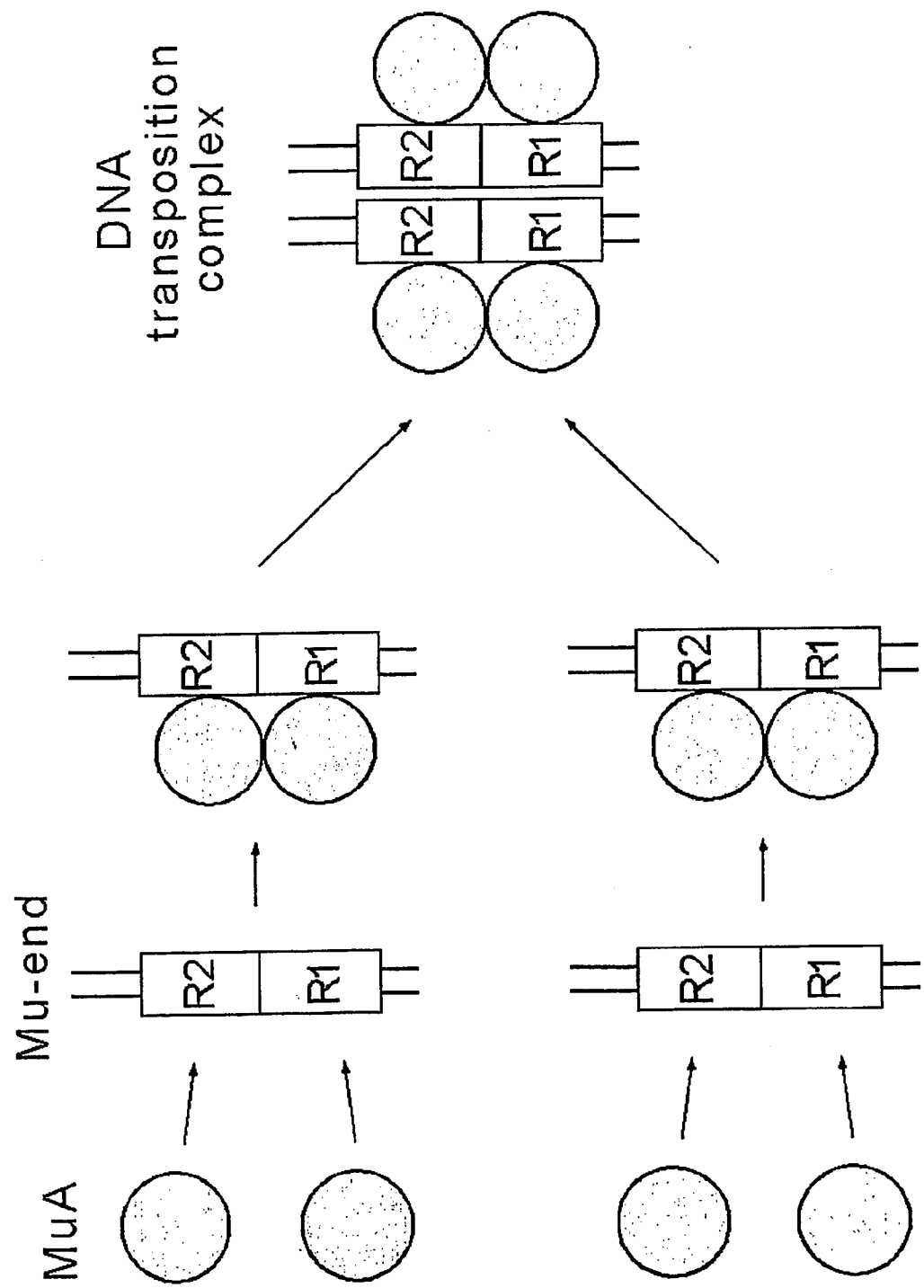
Figure 6:
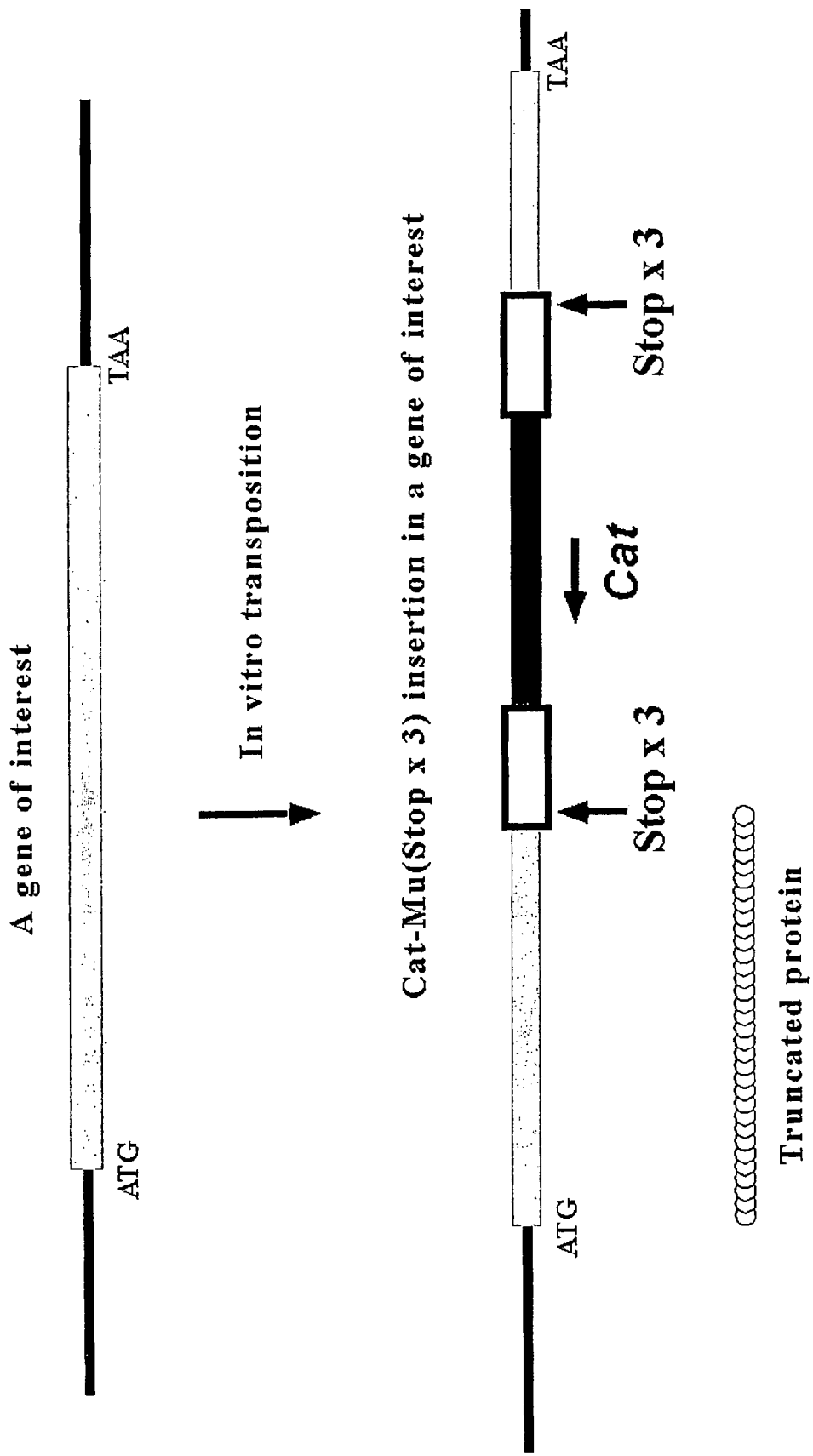
FIG. 6.
Overall strategy for production of C-terminal deletion variants of genes encoding proteins.

Finally, the protein expression analysis (FIG. 4) demonstrated that different deletion variant proteins are produced. Probably due to lack of resolution in the utilised gel system, the supposedly expressed protein was not detectable when the deletion derivative was 8 kDa or smaller. Alternatively, very small versions of the Mso1 protein may be proteolytically degraded inside the cells.

A further embodiment of the invention is a kit providing means for producing deletion derivatives of protein coding nuclear acid sequences. The kit comprises the transposon nucleic acid of the invention. The kit can be packaged in a suitable container and preferably it contains instructions for using the kit.

The results of the invention show that, unexpectedly, it is possible to substantially modify conserved sequences of transposon ends without critically compromising the competence of the modified transposon to assemble transposition complexes and thereafter carry out transposition chemistry. Thus, the invention provides a straightforward solution to the problem of extra amino acids attached in the protein C-terminus of the deletion derivative which could be produced by a conventional transposition system, wherein the transposon used contains the translation stop signals between the transposon ends.

The present invention is further described in the following examples, which are not intended to limit the scope of the invention.

EXAMPLES

Example 1

In Vitro Transposition Reaction

In vitro transposition reaction (25 µl) contained 720 ng cat-Mu(Stop) transposon as a donor, 500 ng plasmid pHis6-MSO1 as a target nucleic acid, 0.2 µg MuA, 25 mM Tris-HCl at pH 8.0, 100 µg/ml BSA, 15% (w/v) glycerol, 0.05% (w/v) Triton X-100, 126 mM NaCl and 10 mM MgCl$_2$. The reaction was carried out at 30° C. for 4 h.

Further details and variables of in vitro Mu transposition are described in Haapa et al. 1999ab and Savilahti et al. 1995, incorporated herein by reference.

Example 2

Generation of a Pool of Mutants with C-terminal Deletions in Mso1

In vitro transposition reactions with Stop-Mu were performed essentially as described in Haapa et al. (1999a) with the exception that they contained 720 ng donor DNA (Stop-Mu×3) and 0,88 µg MuA. Ten reactions were pooled, phenol and chlorophorm extracted, ethanol precipitated, and resuspended in 30 µl of water. Several 1 µl aliquots were electrotransformed, each into 25 µl of DH5α electrocompetent cells, as described (Haapa et al. 1999a). Transposon-containing plasmid clones were selected on LB plates containing Ap and Cm. A total of ~6×10$^5$ colonies were pooled and grown in selective LB-Ap-Cm medium at 37° C. for 3 h after which plasmid DNA was prepared from the pool with Qiagen Plasmid Midi kit. This plasmid preparation was subjected to a XhoI-HindIII double digestion and preparative agarose gel electrophoresis. The DNA fragment corresponding to transposon insertions into the Mso1-containing DNA fragment was isolated with QIAquick Gel Extraction Kit (Qiagen). This fragment was then ligated into the plasmid pH is 6-MSO1 vector XhoI-HindIII backbone to generate a construct pool with transposon insertions located only within the Mso1 gene. After ligation, a pool of plasmids from ~5×10$^4$ colonies was prepared as described above. Approximately 110 000 colonies were pooled. Transposon-carrying Mso1 fragments were cloned into clean vector backbone as described above and approximately 11 000 colonies were pooled in the final C-terminal deletion mutant library. At all stages, the transformants were selected with Ap and Cm.

Example 3

Restriction and Expression Analysis of Deletion Mutants

Mutant clones were analyzed for deletions by BamHI digestion and DNA sequencing. For protein expression analysis, single mutant plasmids were introduced into BL21 (DE3) expression strain. Selective medium was inoculated with o/n culture of bacteria containing mutant plasmid and grown until OD$_{600}$ was 0,4–0,7. Protein expression was induced with 1 mM IPTG for 3 hours and samples were withdrawn for SDS-PAGE analysis. Bacterial lysates were run on 15% gels and stained with GelCode blue stain (Pierce) as recommended by the supplier.

Example 4

Generation of Deletion Mutants with Tn7-Kan (Stop) Transposon

In vitro Tn7 transposition reaction (20 µl) contained 40 ng Tn7-Kan (Stop) transposon (SEQ ID NO:7) as a donor, 100 ng plasmid pUC19 as a target nucleic acid, 7 ng TnsA protein, 10 ng TnsB protein, 20 ng TnsC* protein, 25 mM Tris-HCl at pH 8.0, 50 µg/ml BSA, 2 mM DTT and 2 mM ATP. The reaction mixture was pre-incubated at 37° C. for 10 min before addition of 30 mM magnesium acetate. After the addition the reaction was carried out at 37° C. for 1 h.

The reaction mixture was precipitated with n-butanol to reduce the ionic strength and to concentrate DNA prior to electroporation (Thomas, 1994) and resuspended in 10 µl of water. 5 µl aliquot was electrotransformed into 50 µl of DH10B (Epicentre Technologies) electrocompetent cells. Transposon-containing plasmid clones were selected on LB plates containing kanamycin (20 µg/ml). Approximately 20000 kanamycin resistant colonies were recovered per 1 µg target DNA. Three clones were picked from the transformation plates and grown in LB-Kn medium at 37° C. overnight after which plasmid DNA was prepared from the cultures with QiaPrep Spin Miniprep Kit. The Tn7-Kan (Stop) transposon insertion sites were analyzed by DNA sequencing.

All the mutants carried the translation stop codons in six reading frames and in each case, the integrated transposon was flanked by a 5-bp target site duplication generated in TnsABC*-mediated transposition.

MATERIALS AND METHODS

Bacteria, Media, Enzymes and Reagents

Bacterial cultures were grown in Luria broth supplemented with appropriate antibiotics: ampicillin (Ap) at 100 μg/ml, chloramphenicol (Cm) at 10 μg/ml and kanamycin (Kn) at 20 μg/ml when required. *Escherichia coli* strains were DH5α (Life Technologies), BL21(DE3) (Novagen), and DH10B (Epicentre Technologies). MuA protein was purified in collaboration with Finnzymes (Espoo, Finland) essentially as described (Baker et al. 1993, Haapa et al. 1999a). TnsA, TnsB and TnsC* proteins were purchased from New England Biolabs. Restriction enzymes and T4 DNA ligase were from New England Biolabs and Promega, Triton X-100 from Roche. Standard DNA techniques were performed as described (Sambrook and Russell 2001). Enzymes were used as recommended by suppliers. Sequencing was carried out at the sequencing service unit of the Institute of Biotechnology, University of Helsinki.

Plasmids and Transposons

Plasmid pHis6-MSO1 contains the 633 bp Mso1 gene as an insert (Aalto et al. 1997). The Cat-Mu(Stop) transposon (1254 bp) is a derivative of the Cat-Mu transposon (Haapa et al. 1999a), and they encode resistance to chloramphenicol (FIGS. 1 and 2). The Cat-Mu(Stop)-transposon ends were engineered to carry translation stop signals for both 5'-to-3' directions of dsDNA in all three reading frames. The Tn7-Kan (Stop) transposon is a derivative of the pGPS1.1 transposon (New England Biolabs) and it encodes resistance to kanamycin. The Tn7-Kan (Stop) transposon ends were engineered to carry translation stop signals for both 5'-to-3' directions of dsDNA in all three reading frames. Tn7-Kan (Stop) transposon sequence is 4814 bp in length (SEQ ID NO:7) and nucleotides 3093–4791 set forth in SEQ ID NO:7 constitutes the transposable element. Modified nucleotides were at the positions of 3095, 3097, 3099, 3101, 3103, 4781, 4783, 4785, 4787, and 4789 set forth in SEQ ID NO:7.

Tn7-Kan (Stop) transposon was constructed from PCR-amplified fragments. The transposable fragment was amplified with primers 5' acg gtg agt gag tag aaa ata gtt ggg aac tgg ga 3' (SEQ ID NO:8) and 5' cgt atg agt gag tag aat aaa gtc tta aac tga aca aaa tag a 3' (SEQ ID NO:9) using the plasmid pGPS1.1 as template DNA (New England Biolabs) and the vector fragment was amplified with primers 5' aag tag ctt ttc tgt gac tgg t 3' (SEQ ID NO:10) and 5' gat ggc atg aca gta aga gct 3' (SEQ ID NO:11) using the plasmid pGPS1.1 (New England Biolabs) as template DNA.

Sequencing was performed using the primer 5 '-gct agt tat tgc tca gcg g-3' (SEQ ID NO:5). Sequencing of Tn7-Kan (Stop) transposon insertion sites in pUC19 plasmid was carried out using Model 4200 DNA Sequencer (LI-COR). Sequencing was performed using IRD700-labeled primers 5' agc tgg cga aag ggg gat gtg 3' (SEQ ID NO:12) and 5' tta tgc ttc cgg ctc gta tgt tgt gt 3' (SEQ ID NO:13).

REFERENCES

Aalto, M. K., Jäntti, J., Östling, J., Keränen, S. & Ronne, H. 1997. Mso1p: A yeast protein that functions in secretion and interacts physically and genetically with Sec1p. Proc. Natl. Acad. Sci. USA 94: 7331–7336.

Berg, D. E., and M. M. Howe (ed.). 1989. Mobile DNA. American Society for Microbiology, Washington D.C.

Boeke J. D. 1989. Transposable elements in *Saccharomyces cerevisiae* in Mobile DNA.

Chaconas, G., B. D. Lavoie, and M. A. Watson. 1996. DNA transposition: jumping gene machine, some assembly required. Curr. Biol. 6:817–820.

Coros, C. J., and G. Chaconas. 2001. Effect of mutations in the Mu-host junction region on transpososome assembly. J. Mol. Biol. 310:299–309.

Craig N. L. 1996. Transposon Tn7. Curr. Top. Microbiol. Immunol. 204: 27–48.

Craigie, R., and K. Mizuuchi. 1987. Transposition of Mu DNA: joining of Mu to target DNA can be uncoupled from cleavage at the ends of Mu. Cell. 51:493–501.

Devine, S. E. and Boeke, J. D., Nucleic Acids Research, 1994, 22(18): 3765–3772.

Groenen, M. A. M., and P. van den Putte. 1986. Analysis of the ends of bacteriophage Mu using site-directed mutagenesis. J. Mol. Biol. 189:597–602.

Groenen, M. A. M., E. Timmers, and P. van den Putte. 1985. DNA sequences at the ends of the genome of bacteriophage Mu essential for transposition. Proc. Natl. Acad. Sci. USA. 82:2087–2091.

Haapa, S., S. Taira, E. Heikkinen, and H. Savilahti. 1999a. An efficient and accurate integration of mini-Mu transposons in vitro: a general methodology for functional genetic analysis and molecular biology applications. Nucleic Acids Res. 27:2777–2784.

Haapa, S., S. Suomalainen, S. Eerikäinen, M. Airaksinen, L. Paulin, and H. Savilahti. 1999b. An efficient DNA sequencing strategy based on the bacteriophage Mu in vitro DNA transposition reaction. Genome Res. 9:308–315.

Haapa-Paananen, S., H. Rita, and H. Savilahti. 2002. DNA tranposition of bacteriophage Mu. A quantitative analysis of target site selection in vitro. J. Biol. Chem. 277: 2843–2851.

Hayes, F., and B. Hallet. 2000. Pentapeptide scanning mutagenesis: encouraging old proteins to execute unusual tricks. Trends Microbiol. 8:571–577.

Ichikawa H. and Ohtsubo E., J. Biol. Chem., 1990, 265(31): 18829–32.

Kahman, R., and D. Kamp. 1979. Nucleotide sequences of the attachment sites of bacteriophage Mu. Nature 280: 247–250.

Kaufman P. and Rio D. C. 1992. Cell, 69(1): 27–39.

Kleckner N., Chalmers R. M., Kwon D., Sakai J. and Bolland S. Tn10 and IS10 Transposition and chromosome rearrangements: mechanism and regulation in vivo and in vitro. Curr. Top. Microbiol. Immunol., 1996, 204: 49–82.

Lampe D. J., Churchill M. E. A. and Robertson H. M., EMBO J., 1996, 15(19): 5470–5479.

Laurent, L. C., M. N. Olsen, R. A. Crowley, H. Savilahti, and P. O. Brown. 2000. Functional characterization of the human immunodeficiency virus type 1 genome by genetic footprinting. J. Virol. 74:2760–2769.

Lee, I., and R. M. Harshey. 2001. Importance of the conserved CA dinucleotide at Mu termini. J. Mol. Biol. 314:433–444.

Mizuuchi, K. 1992. Transpositional recombination: mechanistic insights from studies of Mu and other elements. Annu. Rev. Biochem. 61:1011–1051.

Ohtsubo E. & Sekine Y. Bacterial insertion sequences. Curr. Top. Microbiol. Immunol., 1996, 204:1–26.

Park B. T., Jeong M. H. and Kim B. H., Taehan Misaengmul Hakhoechi, 1992, 27(4): 381–9.

Sambrook, J., E. F. Fritch, and T. Maniatis. 1989. Molecular Cloning: a laboratory manual, 2nd ed. Cold Spring Harbor Laboratory Press, Cold Spring Harbor, N. Y.

Sambrook, J. and D. W. Russell, 2001. Molecular Cloning: a laboratory manual, 3rd ed. Cold Spring Harbor Laboratory Press, Cold Spring Harbor, N.Y.

Savilahti, H. and K. Mizuuchi. 1996. Mu transpositional recombination: donor DNA cleavage and strand transfer in trans by the Mu transposase. Cell 85:271–280.

Savilahti, H., P. A. Rice, and K. Mizuuchi. 1995. The phage Mu transpososome core: DNA requirements for assembly and function. EMBO J. 14:4893–4903.

Sherratt, D. J. (ed.). 1995. Mobile genetic elements. Oxford University Press, Oxford, U.K.

Surette, M. G., S. J. Buch, and G. Chaconas. 1987. Transpososomes: stable protein-DNA complexes involved in the in vitro transposition of bacteriophage Mu DNA. Cell 49: 253–262.

Taira, S., J. Tuimala, E. Roine, E. L. Nurmiaho-Lassila, H. Savilahti, and M. Romantschuk. 1999. Mutational analysis of the *Pseudomionas syringae* pv. tomato hrpA gene encoding Hrp pilus subunit. Mol. Microbiol. 34:737–744.

Thomas, M. R. 1994. Simple, effective cleanup of DNA ligation reactions prior to electro-transformation of *E. coli*. BioTechniques 16:988.

Varmus H and Brown. P. A. 1989. Retroviruses, in Mobile DNA. Berg D. E. and Howe M. eds. American society for microbiology, Washington D.C. pp. 53–108.

Vilen, H., S. Eerikäinen, J. Tornberg, M. Airaksinen, and H. Savilahti. 2001. Construction of gene-targeting vectors: a rapid Mu in vitro DNA transposition-based strategy generating null, potentially hypomorphic, and conditional alleles. Transgenic Res. 10:69–80.

Vos J. C., Baere I. And Plasterk R. H. A., Genes Dev., 1996, 10(6): 755–61.

Wei, S. Q., K. Mizuuchi, and R. Craigie. 1997. A large nucleoprotein assembly at the ends of the viral DNA mediates retroviral DNA integration. EMBO J. 16:7511–7520.

We claim:

1. A transposon nucleic acid having two transposon end sequences, at least one of which comprises a genetically engineered translation stop signal in three reading frames wherein one part of said translation stop signal is within a transposon end binding sequence recognized by a transposase, and another part of said translation stop signal is between said transposon end binding sequence and the distal end of said transposon end sequence.

2. The transposon nucleic acid according to claim 1, wherein said transposon nucleic acid contains a selectable marker and/or a reporter gene.

3. The transposon nucleic acid according to claim 1 or 2, wherein said one transposon end sequence is a Mu or Tn7 end sequence.

4. The transposon nucleic acid according to claim 3, wherein said transposon end binding sequence within said one Mu transposon end sequence is the Mu R-end binding sequence.

5. The transposon nucleic acid according to claim 4, wherein said transposon sequence is set forth in SEQ ID NO:1, SEQ ID NO:2 or SEQ ID NO:5.

6. The transposon nucleic acid according to claim 3, wherein said transposon sequence is set forth in SEQ ID NO:7.

7. The transposon nucleic acid according to claim 1, further comprising a genetically engineered restriction enzyme site.

8. A method of producing a deletion derivative of a polypeptide coding nucleic acid comprising the steps of:
 (a) performing a transposition reaction in the presence of a target nucleic acid containing a nucleic acid encoding a polypeptide of interest in the presence of a transposon containing a transposon nucleic acid having two transposon end sequences at least one of which comprises a genetically engineered translation stop signal in three reading frames wherein one part of said translation stop signal is within a transposon end binding sequence recognized by a transposase, and another part of said translation stop signal is between said transposon end binding sequence and the distal end of said transposon end sequences and
 (b) recovering the target nucleic acid having said transposon incorporated in said polypeptide-encoding nucleic acid.

9. The method according to claim 8 further comprising a step of (c) expressing said polypeptide-encoding nucleic acid having said transposon incorporated.

10. The method according to claim 8 or 9, wherein said transposon nucleic acid further comprises a selectable marker and/or a reporter gene.

11. A kit for producing deletion derivatives of polypeptide-encoding nucleic acids comprising the transposon nucleic acid of claim 1.

* * * * *

SEQUENCE LISTING

```
<160> NUMBER OF SEQ ID NOS: 16

<210> SEQ ID NO 1
<211> LENGTH: 54
<212> TYPE: DNA
<213> ORGANISM: Artificial Sequence
<220> FEATURE:
<223> OTHER INFORMATION: Description of Artificial Sequence: Modified
      Mu end sequence

<400> SEQUENCE: 1
gatctgattg attgaacgaa aaacgcgaaa gcgtttcacg ataaatgcga aaac         54

<210> SEQ ID NO 2
<211> LENGTH: 1254
<212> TYPE: DNA
<213> ORGANISM: Artificial Sequence
<220> FEATURE:
<223> OTHER INFORMATION: Description of Artificial Sequence: Modified
      Mu transposon

<400> SEQUENCE: 2
gatctgattg attgaacgaa aaacgcgaaa gcgtttcacg ataaatgcga aaacggatcc      60
tatcgtcaat tattacctcc acggggagag cctgagcaaa ctggcctcag gcatttgaga    120
agcacacggt cacactgctt ccggtagtca ataaaccggt aaaccagcaa tagacataag    180
cggctattta acgaccctgc cctgaaccga cgaccgggtc gaatttgctt tcgaatttct    240
gccattcatc cgcttattat cacttattca ggcgtagcaa ccaggcgttt aagggcacca    300
ataactgcct taaaaaaatt acgccccgcc ctgccactca tcgcagtact gttgtaattc    360
attaagcatt ctgccgacat ggaagccatc acaaacggca tgatgaacct gaatcgccag    420
cggcatcagc accttgtcgc cttgcgtata atatttgccc atggtgaaaa cggggggcgaa    480 gaagttgtcc atattggcca cgtttaaatc aaaactggtg aaactcaccc agggattggc    540
tgagacgaaa aacatattct caataaaccc tttagggaaa taggccaggt tttcaccgta    600
acacgccaca tcttgcgaat atatgtgtag aaactgccgg aaatcgtcgt ggtattcact    660
ccagagcgat gaaaacgttt cagtttgctc atggaaaacg gtgtaacaag ggtgaacact    720
atcccatatc accagctcac cgtctttcat tgccatacgt aattccggat gagcattcat    780
```

```
caggcgggca agaatgtgaa taaaggccgg ataaaacttg tgcttatttt tctttacggt    840
ctttaaaaag gccgtaatat ccagctgaac ggtctggtta taggtacatt gagcaactga    900
ctgaaatgcc tcaaaatgtt ctttacgatg ccattgggat atatcaacgg tggtatatcc    960
agtgattttt ttctccattt tagcttcctt agctcctgaa aatctcgaca actcaaaaaa    1020
tacgcccggt agtgatctta tttcattatg gtgaaagttg gaacctctta cgtgccgatc    1080
aacgtctcat tttcgccaaa agttggccca gggcttcccg gtatcaacag ggacaccagg    1140
atttatttat tctgcgaagt gatcttccgt cacaggtatt tattcggtcg aaaaggatcc    1200
gttttcgcat ttatcgtgaa acgctttcgc gtttttcgtt caatcaatca gatc          1254

<210> SEQ ID NO 3
<211> LENGTH: 54
<212> TYPE: DNA
<213> ORGANISM: Bacteriophage Mu

<400> SEQUENCE: 3
gatctgaagc ggcgcacgaa aaacgcgaaa gcgtttcacg ataaatgcga aaac           54

<210> SEQ ID NO 4
<211> LENGTH: 54
<212> TYPE: DNA
<213> ORGANISM: Artificial Sequence
<220> FEATURE:
<223> OTHER INFORMATION: Description of Artificial Sequence: Modified Mu
      end sequence

<400> SEQUENCE: 4
gatctgcggc cgcgcacgaa aaacgcgaaa gcgtttcacg ataaatgcga aaac           54

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Modified Mu
      end sequence without 5' overhang

<400> SEQUENCE: 5
tgattgattg aacgaaaaac gcgaaagcgt ttcacgataa atgcgaaaac               50

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Sequencing
      primer

<400> SEQUENCE: 6
gctagttatt gctcagcgg                                                  19

<210> SEQ ID NO 7
<211> LENGTH: 4814
<212> TYPE: DNA
<213> ORGANISM: Artificial Sequence
<220> FEATURE:
<223> OTHER INFORMATION: Description of Artificial Sequence: Modified
      Tn7 transposon

<400> SEQUENCE: 7
ggtaccctgt gaatgcgcaa accaacccct tggcagaacat atccatcgcg tccgccatct    60
ccagcagccg cacgcggcgc atctcgggca gcgttgggtc ctggccacgg gtgcgcatga    120
```

-continued

```
tcgtgctcct gtcgttgagg acccggctag gctggcgggg ttgccttact ggttagcaga      180
atgaatcacc gatacgcgag cgaacgtgaa gcgactgctg ctgcaaaacg tctgcgacct      240
gagcaacaac atgaatggtc ttcggttccc gtgtttcgta aagtctggaa acgcggaagt      300
cagcgccctg caccattatg ttccggatct atgtcgggtg cggagaaaga ggtaatgaaa      360
tggcagatcc ctggcttgtt gtccacaacc gttaaacctt aaaagcttta aaagccttat      420
atattctttt ttttcttata aaacttaaaa ccttagaggc tatttaagtt gctgatttat      480
attaatttta ttgttcaaac atgagagctt agtacgtgaa acatgagagc ttagtacgtt      540
agccatgaga gcttagtacg ttagccatga gggtttagtt cgttaaacat gagagcttag      600
tacgttaaac atgagagctt agtacgtgaa acatgagagc ttagtacgta ctatcaacag      660
gttgaactgc tgatcttcgg atctatgtcg ggtgcggaga agaggtaat gaaatggcag      720 atccctggct tgttgtccac aaccgttaaa ccttaaaagc tttaaaagcc ttatatattc      780
ttttttttct tataaaactt aaaacctag aggctattta agttgctgat ttatattaat      840
tttattgttc aaacatgaga gcttagtacg tgaaacatga gcttagta cgttagccat      900 gagagcttag tacgttagcc atgagggttt agttcgttaa acatgagagc ttagtacgtt      960
aaacatgaga gcttagtacg tgaaacatga gcttagta cgtactatca acaggttgaa     1020
ctgctgatct tcggatctat gtcgggtgcg gagaaagagg taatgaaatg gcatccggat     1080
ctgcatcgca ggatgctgct ggctaccctg tggaacacct acatctgtat taacgaagca     1140
ttattgaagc atttatcagg gttattgtct catgagcgga tacatatttg aatgtattta     1200
gaaaaataaa caaatagggg ttccgcgcac atttccccga aaagtgccac ctgacgtcta     1260
agaaaccatt attatcatga cattaaccta taaaaatagg cgtatcacga ggcccttcg      1320 tcttcaagaa ttctcatgtt tgacagctta tcatcgataa gctttaatgc ggtagtttat     1380
cacagttaaa ttgctaacgc agtcaggcac cgtgtatgaa atctaacaat gcgctcatcg     1440
tcatcctcgg caccgtcacc ctggatgctg taggcatagg cttggttatg ccggtactgc     1500
cgggcctctt gcgggatatc gtccattccg acagcatcgc cagtcactat ggcgtgctgc     1560
tagcgctata tgcgttgatg caatttctat gcgcacccgt tctcggagca ctgtccgacc     1620
gctttggccg ccgcccagtc ctgctcgctt cgctacttgg agccactatc gactacgcga     1680
tcatggcgac cacacccgtc ctgtggatcc tctacgccgg acgcatcgtg gccggcatca     1740
ccggcgccac aggtgcggtt gctgcgcct atatcgccga catcaccgat ggggaagatc     1800
gggctcgcca cttcgggctc atgagcgctt gtttcggcgt gggtatggtg caggccccg      1860 tggccggggg actgttgggc gccatctcct gcatgcacc attccttgcg gcggcggtgc      1920
tcaacggcct caacctacta ctgggctgct tcctaatgca ggagtcgcat aagggagagc     1980
gtcgaccgat gcccttgaga gccttcaacc cagtcagctc cttccggtgg gcgcggggca     2040
tgactatcgt cgccgcactt atgactgtct tctttatcat gcaactcgta ggacaggtgc     2100
cggcagcgct ctgggtcatt ttcggcgagg accgctttcg ctggagcgcg acgatgatcg     2160
gcctgtcgct tgcggtattc ggaatcttgc acgccctcgc tcaagccttc gtcactggtc     2220
ccgccaccaa acgtttcggc gagaagcagg ccattatcgc cggcatggcg gccgacgcgc     2280
tgggctacgt cttgctggcg ttcgcgacgc gaggctggat ggccttcccc attatgattc     2340
ttctcgcttc cggcggcatc gggatgcccg cgttgcaggc catgctgtcc aggcaggtag     2400
atgacgacca tcaggacag cttcaaggat cgctcgcggc tcttaccagc ctaacttcga     2460
tcattggacc gctgatcgtc acggcgattt atgccgcctc ggcgagcaca tggaacgggt     2520
```

```
tggcatggat tgtaggcgcc gccctatacc ttgtctgcct cccgcgttg cgtcgcggtg    2580 catggagccg ggccacctcg acctgaatgg aagccggcgg cacctcgcta acggattcac    2640
cactccaaga attggagcca atcaattctt gcggagaact gtgaatgcgc aaaccaaccc    2700
ttggcagaac atatccatcg cgtccgccat ctccagcagc cgcacgcggc gcatctcggg    2760
cagcgttggg tcctgggctg gcattgaccc tgagtgattt ttctctggtc ccgccgcatc    2820
cataccgcca gttgtttacc ctcacaacgt tccagtaacc gggcatgttc atcatcagta    2880
acccgtatcg tgagcatcct ctctcgtttc atcggtatca ttaccccat gaacagaaat    2940 cccccttaca cggaggcatc agtgaccaaa caggaaaaaa ccgcccttaa catggcccgc    3000
tttatcagaa gccagacatt aacgcttctg gagaaactca acgagctgga cgcggatgaa    3060
caggcagagc tcttactgtc atgccatccg tatgagtgag tagaataaag tcttaaactg    3120
aacaaaatag atctaaacta tgacaataaa gtcttaaact agacagaata gttgtaaact    3180
gaaatcagtc cagttatgct gtgaaaaagc atactggact tttgttatgg ctaaagcaaa    3240
ctcttcattt tctgaagtgc aaattgcccg tcgtattaaa gagggcgtg gggtcgacgc    3300 ggccgctaac tataacggtc ctaaggtagc gagtttaaac gatatcggat ccggccgccg    3360
ctgaggtctg cctcgtgaag aaggtgttgc tgactcatac caggcctgaa tcgccccatc    3420
atccagccaa aaagtgaggg agccacggtt gatgagagct tgttgtagg tggaccagtt    3480 ggtgattttg aacttttgct ttgccacgga acggtctgcg ttgtcgggaa gatgcgtgat    3540
ctgatccttc aactcagcaa gagttcgatt tattcaacaa agccgccgtc ccgtcaagtc    3600
agcgtaatgc tctgccagtg ttacaaccaa ttaaccaatt ctgattagaa aaactcatcg    3660
agcatcaaat gaaactgcaa tttattcata tcaggattat caataccata tttttgaaaa    3720
agccgtttct gtaatgaagg agaaaactca ccgaggcagt tccataggat ggcaagatcc    3780
tggtatcggt ctgcgattcc gactcgtcca acatcaatac aacctattaa tttcccctcg    3840
tcaaaaataa ggttatcaag tgagaaatca ccatgagtga cgactgaatc cggtgagaat    3900
ggcaaaagct tatgcatttc tttccagact tgttcaacag gccagccatt acgctcgtca    3960
tcaaaatcac tcgcatcaac caaaccgtta ttcattcgtg attgcgcctg agcgagacga    4020
aatacgcgat cgctgttaaa aggacaatta caaacaggaa tcgaatgcaa ccggcgcagg    4080
aacactgcca gcgcatcaac aatatttca cctgaatcag gatattcttc taatacctgg    4140
aatgctgttt tcccggggat cgcagtggtg agtaaccatg catcatcagg agtacggata    4200
aaatgcttga tggtcggaag aggcataaat tccgtcagcc agtttagtct gaccatctca    4260
tctgtaacat cattggcaac gctacctttg ccatgtttca gaaacaactc tggcgcatcg    4320
ggcttcccat acaatcgata gattgtcgca cctgattgcc cgacattatc gcgagcccat    4380
ttatacccat ataaatcagc atccatgttg gaatttaatc gcggcctcga gcaagacgtt    4440
tcccgttgaa tatggctcat aacacccctt gtattactgt ttatgtaagc agacagtttt    4500
attgttcatg atgatatatt tttatcttgt gcaatgtaac atcagagatt ttgagacaca    4560
acgtggctta ctaggatccg atatcattta aatctaggga taacagggta atactagtgt    4620
cgaccaacca gataagtgaa atctagttcc aaactatttt gtcattttta attttcgtat    4680
tagcttacga cgctacaccc agttcccatc tattttgtca ctcttcccta aataatcctt    4740
aaaaactcca tttccaccccc tcccagttcc caactatttt ctactcactc accgtaagat    4800
gcttttctgt gact                                                     4814
```

```
<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 8
acggtgagtg agtagaaaat agttgggaac tggga                              35

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 9
cgtatgagtg agtagaataa agtcttaaac tgaacaaaat aga                     43

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 10
aagtagcttt tctgtgactg gt                                            22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 11
gatggcatga cagtaagagc t                                             21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 12
agctggcgaa aggggatgt g                                              21

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 13
ttatgcttcc ggctcgtatg ttgtgt                                        26
```

```
<210> SEQ ID NO 14
<211> LENGTH: 50
<212> TYPE: DNA
<213> ORGANISM: Bacteriophage Mu

<400> SEQUENCE: 14
gttttcgcat ttatcgtgaa acgctttcgc gtttttcgtg cgccgcttca           50

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Modified Mu
      end sequence

<400> SEQUENCE: 15
gttttcgcat ttatcgtgaa acgctttcgc gtttttcgtg cgcggccgca           50

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Modified Mu
      end sequence

<400> SEQUENCE: 16
gttttcgcat ttatcgtgaa acgctttcgc gtttttcgtt caatcaatca           50
```